United States Patent
Smith

(10) Patent No.: US 10,537,566 B2
(45) Date of Patent: Jan. 21, 2020

(54) COMBINATIONS COMPRISING SIPONIMOD AND LAQUINIMOD FOR THE TREATMENT OF MULTIPLE SCLEROSIS

(71) Applicant: Paul Alfred Smith, Saint Louis-Strasse (CH)

(72) Inventor: Paul Alfred Smith, Saint Louis-Strasse (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/517,280

(22) PCT Filed: Oct. 14, 2015

(86) PCT No.: PCT/IB2015/057870
§ 371 (c)(1),
(2) Date: Apr. 6, 2017

(87) PCT Pub. No.: WO2016/059571
PCT Pub. Date: Apr. 21, 2016

(65) Prior Publication Data
US 2017/0304289 A1    Oct. 26, 2017

Related U.S. Application Data

(60) Provisional application No. 62/064,537, filed on Oct. 16, 2014.

(51) Int. Cl.
*A61K 31/4704* (2006.01)
*A61K 31/397* (2006.01)
(52) U.S. Cl.
CPC ........ *A61K 31/4704* (2013.01); *A61K 31/397* (2013.01)
(58) Field of Classification Search
None
See application file for complete search history.

(56) References Cited

FOREIGN PATENT DOCUMENTS

| CN | 103260624 A | 8/2013 |
|----|-------------|--------|
| CN | 103974704 A | 8/2014 |
| WO | 2013/055907 A1 | 4/2013 |
| WO | 2014/127139 A1 | 8/2014 |
| WO | 2014161606 A1 | 10/2014 |

OTHER PUBLICATIONS

Haggiag, S., et al., Ther. Adv. Neurol. Disord., 6:343. (Year: 2013).*
Selmaj, et al., Lancet Neurol., 12:756. (Year: 2013).*
ClinicalTrials identifier NCT01665144. (Year: 2012).*
Curtin F et al: "Novel therapeutic options for multiple sclerosis", Expert Review of Clinical Pharmacology, vol. 7, No. 1 Jan. 10, 2014 (Jan. 10, 2014), pp. 91-104, XP008178151.
U.E. Williams et al: "Disease modifying therapy in multiple scloerosis", International Scholarly Research Notices, vol. 63, No. 12, Jan. 1, 2014 (Jan. 1, 2014), pp. S15-S17, XP055229370.
Kappos Ludwig; et al: "Siponimod (BAF312) for the Treatment of Secondary Progressive Multiple Sclerosis: Design of the Phase 3 EXPAND Trial", Neurology, vol. 80, No. Suppl., Feb. 1, 2013 (Feb. 1, 2013), p. J07126, XP055197407, us ISSN: 0028-3878.
Pan Shifeng, "Discovery of BAF312 (Siponimod), a Potent and Selective S1P Receptor Modulator", ACS Medicinal Chemistry Letters, 2013, vol. 4, pp. 333-337.

\* cited by examiner

*Primary Examiner* — Michael Barker
(74) *Attorney, Agent, or Firm* — Laura Madden; Novartis AG

(57) ABSTRACT

The present invention relates to combinations and pharmaceutical compositions comprising siponimod and laquinimod, and the use of said combinations and/or compositions for the treatment of multiple sclerosis, particularly secondary progressive multiple sclerosis.

6 Claims, 4 Drawing Sheets

COMBINATIONS COMPRISING SIPONIMOD AND LAQUINIMOD FOR THE TREATMENT OF MULTIPLE SCLEROSIS

FIELD OF THE INVENTION

The present invention relates to combinations and pharmaceutical compositions comprising siponimod and laquinimod, and to the use of said combinations and/or compositions as medicaments for the treatment of multiple sclerosis.

BACKGROUND

Multiple Sclerosis: Relapsing and Progressive Forms

Multiple sclerosis (MS) is a neurological disease affecting more than 1 million people worldwide. It is the most common cause of neurological disability in young and middle-aged adults and has a major physical, psychological, social and financial impact on subjects and their families, friends and bodies responsible for health care.

It is generally assumed that, initially, MS is mediated by some autoimmune process possibly triggered by infection and superimposed upon a genetic predisposition. It is a chronic inflammatory condition that damages the myelin of the central nervous system (CNS). The pathogenesis of MS is characterized by the infiltration of lymphocytes (i.e. autoreactive T-cells) from the circulation directed against myelin antigens into the CNS. In addition to the inflammatory phase in MS, axonal loss occurs early in the course of the disease and can be extensive over time, leading to the subsequent development of progressive, permanent, neurologic impairment and, frequently, severe disability. Symptoms associated with the disease include fatigue, spasticity, ataxia, weakness, bladder and bowel disturbances, sexual dysfunction, pain, tremor, paroxysmal manifestations, visual impairment, psychological problems and cognitive dysfunction.

Various MS disease stages and/or types are described in Multiple Sclerosis Therapeutics (Duntiz, Ed. Rudick and Goodkin, London: Taylor & Francis, 1999). Among them, relapsing-remitting multiple sclerosis (RRMS) is the most common form at the time of initial diagnosis. At the time of diagnosis, between 80% and 90% of MS patients have RRMS. This form of MS is characterized by recurring relapses, i.e. acute episodes, of neurological symptoms followed by recovery periods (remissions). In around 80% of the patients with RRMS, this form later develops to secondary progressive multiple sclerosis (SPMS) around 19 years after disease onset.

When a patient has developed SPMS, disease progression proceeds with or without occasional relapses with no or only minor remissions between relapses and is characterized symptomatically by a continuous worsening of disability, independent of relapses (if present). Symptoms that indicate a shift towards SPMS include a steady increase in weakness and incoordination; stiff, tight leg muscles; bowel and bladder problems; greater fatigue, depression, and problems of thinking. In general, the number of inflammatory infiltrates decreases, while neurodegeneration becomes a more prominent feature of SPMS.

However, recently it has been discovered that inflammation in the brain does not only occur in RRMS patients, but also in SPMS patients. Furthermore, in patients with SPMS, inflammation in the meninges can be found. These immune aggregates are T-cell and B-cell rich structures. Cortical tissue next to these structures shows a significantly increased pathology (Serafini et al, 2004). It has been found that the extent of inflammation in the meninges correlates with the amount of neurodegeneration; furthermore these structures have been reported in SPMS patients only—they have not been observed in RRMS or PPMS patients (Magliozzi et al 2007). SPMS patients with post-mortem identified CNS aggregates had an early disease onset, faster conversion to progressive MS and rapid morbitity (Howell et al 2011). Thus, inflammation seems to drive tissue degeneration at least in some patients.

Although RRMS can be unpredictable, the pattern of clear attacks followed by recovery typically is consistent. With SPMS, relapses tend to be less distinct and, depending on many factors, they may happen less often or not at all. However, when relapses do occur in SPMS patients, their recovery normally is not as complete as in RRMS patients.

Although several drugs are known for treating RRMS, SPMS is in general more difficult to treat.

Marketed Monotherapies for MS

There are currently a number of disease-modifying medications approved for use in relapsing MS (RMS). These include the non-oral medications interferon beta 1-a (e.g. Avonex®, Rebif®, Plegridy®), interferon beta 1-b (Betaseron®, Extavia®), glatiramer acetate (Copaxone®), mitoxantrone (Novantrone®), natalizumab (Tysabri®) and alemtuzumab (Lemtrada®); and the oral medications fingolimod (Gilenya®), teriflunomide (Aubagio®) and dimethyl fumarate (Tecfidera®). Most of these medications are believed to act as immunomodulators. Mitoxantrone and natalizumab are believed to act as immunesuppressants. However, the mechanisms of action of each have been only partly elucidated.

Other therapeutic approaches include symptomatic treatment (which refers to all therapies applied to improve the symptoms caused by the disease) and treatment of acute relapses with corticosteroids. While steroids do not affect the course of MS over time, they can reduce the duration and severity of attacks in some subjects.

Examples of Monotherapies for MS being Under Development

Siponimod

Siponimod belongs to the class of drugs called sphingosine 1-phosphate (S1P) receptor modulators. Another member of said group is fingolimod (Gilenya®) which is marketed to treat RRMS.

Siponimod has been tested in a phase II trial where it showed dose-dependent efficacy in treating RRMS (i.e. the BOLD trial) when given oral at a doses of 0.25 mg, 0.5 mg, 1.25 mg, 2 mg and 10 mg.

S1P receptor modulators are known to block the capacity of leukocytes to migrate from lymph nodes into the peripheral blood. It can sequester lymphocytes in lymph nodes, preventing them from moving to the central nervous system for auto-immune responses in multiple sclerosis.

However, siponimod crosses the blood-brain-barrier and may also have a direct beneficial effect on cells in the CNS. S1P receptor modulators have been reported to stimulate the repair process of glial cells and precursor cells after injury (Alejandro Horga et al, Expert Rev Neurother 8(5), 699-714, 2008) which could form the basis of efficacy in SPMS.

Laquinimod

Laquinimod has been suggested as an oral formulation for the treatment of RRMS. It has been tested in two phase III trials where it showed efficacy in treating RRMS (i.e. the BRAVO trial and the ALLEGRO trial) when given oral at a dose of 0.6 mg once daily over a period of 24 months.

Laquinimod and its sodium salt form are described, e.g. in U.S. Pat. No. 6,077,851. The mechanism of action of laquinimod is not fully understood.

Combination Therapy of Disease-Modifying Medications

The administration of two drugs to treat a given condition, such as MS, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug.

In WO2013055907, a combination comprising the experimental drug laquinimod and the marketed drug fingolimod is tested in an animal model for RRMS (i.e. MOG-induced experimental autoimmune encephalomyelitis (EAE) in the C57Bl/6 strain of mice). This model is an established model to test the efficacy of medicines as preventive agents to treat RRMS. A combination of 10 mg/kg of laquinimod with 0.3 mg/kg of fingolimod showed a synergistic effect in preventing disease severity.

However, in other examples of drug combinations, lack of synergy or even antagonism was seen and other unwanted side effects were reported.

The combined administration of fingolimod and interferon has been shown to abrogate the clinical effectiveness of either therapy (Brod et al, Annals of Neurology, 47, 127-131, 2000). In another experiment, it was reported that the addition of prednisone in combination therapy with interferon beta antagonized its up-regulator effect (Salama et al, Multiple Sclerosis, 9, 28-31, 2003).

In one example, the combination of natalizumab and interferon beta 1-a was observed to increase the risk of unanticipated side effects (Rudick et al, New England Journal of Medicine, 354, 911-923, 2006; Kleinschmidt-DeMasters, New England Journal of Medicine, 353, 369-379, 2005; Langer-Gould, New England Journal of Medicine, 353, 369-379, 2005).

Thus, when two drugs are administered to treat the same condition, it is unpredictable whether each will complement, have no effect on, or interfere with, the therapeutic activity of the other in a subject. Not only may the interaction between two drugs affect the intended therapeutic activity of each drug, but the interaction may increase the levels of toxic metabolites. The interaction may also heighten or lessen the side effects of each drug. Hence, upon administration of two drugs to treat a disease, it is unpredictable what change will occur in the negative side profile of each drug. Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs.

Therefore, the state of the art at the time of filing is that the effects of combination therapy of two specific drugs, in particular siponimod and laquinimod, cannot be predicted until the results of a combination study are available.

There is a need to provide effective medicaments for the treatment of autoimmune diseases, e.g. SPMS.

SUMMARY OF THE INVENTION

Surprisingly, combination therapy of siponimod and laquinimod offers significant benefits in the treatment, prevention or delay of progression of autoimmune diseases, particularly SPMS.

Surprisingly it was found that combinations comprising siponimod and laquinimod are effective to treat MS in a damaged CNS (e.g. after disease outbreak/a relapse has occurred) and synergistically reduce the number of lymphocytes. Therefore it is expected e.g. that combinations comprising siponimod and laquinimod (i) are able to lessen inflammatory events, e.g. inflammation in the meninges, in the CNS of SPMS patients and/or (ii) effectively reduce the number and/or severity of relapses in SPMS patients.

Surprisingly it was found that there was no evidence of drug-drug interactions. The synergistic activity of the combination therapy of the invention represents an enhanced biological response.

Surprisingly it was found that the effect of the treatment of the combination comprising siponimod and laquinimod has a faster onset when compared with the monotheraphy with either siponimod or laquinimod.

DETAILED DESCRIPTION OF THE INVENTION

Figure 1:
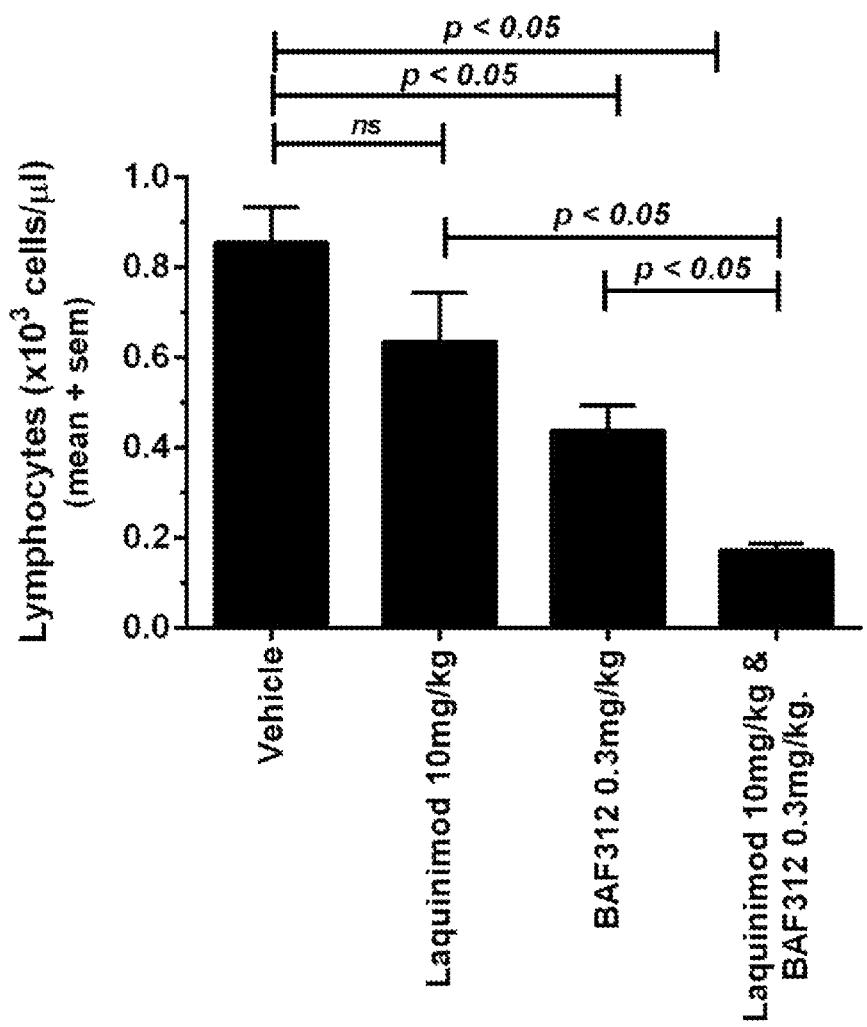
FIG. 1: Use of siponimod and laquinimod to reduce lymphocytes in MOG/CFA/*Pertussis* toxin-immunized C57/Bl6 mice.

The invention provides a combination comprising siponimod and laquinimod for use in the treatment, prevention or delay of progression of secondary progressive multiple sclerosis.

A further aspect of the invention relates to a combination comprising siponimod and laquinimod for the use as a medicament.

Yet a further aspect of the invention relates to a combination comprising siponimod and laquinimod.

Yet a further aspect of the invention relates to a pharmaceutical composition comprising siponimod and laquinimod and at least one pharmaceutically acceptable carrier.

Yet a further aspect of the invention relates to a method for the treatment, prevention or delay of progression of secondary progressive multiple sclerosis in a subject in need of such treatment, which comprises administering to said subject a therapeutically effective amount of a combination comprising siponimod and laquinimod.

Yet a further aspect of the invention relates to a method for the treatment, prevention or delay of progression of secondary progressive multiple sclerosis in a subject in need of such treatment, which comprises (i) diagnosing said secondary progressive multiple sclerosis in said subject, and (ii) administering to said subject a therapeutically effective amount of a combination comprising siponimod and laquinimod.

For the avoidance of doubt, it is hereby stated that the information disclosed earlier in this specification under the heading "Background" is relevant to the invention and is to be read as part of the disclosure of the invention.

As used herein, and unless stated otherwise, each of the following terms shall have the definition set forth below.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification (which term encompasses both the description and the claims) is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

"Siponimod" as used herein is understood to comprise the compound of formula (I)

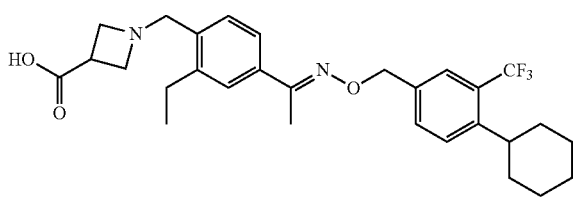

as well as the pharmaceutically acceptable salts, polymorphs, solvates and/or hydrates thereof. Siponimod as used herein has the IUPAC-name 1-{4-[1-((E)-4-cyclohexyl-3-trifluoromethyl-benzyloxyimino)-ethyl]-2-ethyl-benzyl}-azetidine-3-carboxylic acid (BAF312). In a preferred embodiment of the invention, siponimod is present in the form of siponimod free base or siponimod salt. Examples of pharmaceutically acceptable salts of siponimod include salts with inorganic acids, such as hydrochloride, hydrobromide and sulfate, salts with organic acids, such as acetate, fumarate, hemifumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. In a preferred embodiment siponimod is siponimod hemifumarate.

"Laquinimod" as used herein is understood to comprise the compound of formula (II)

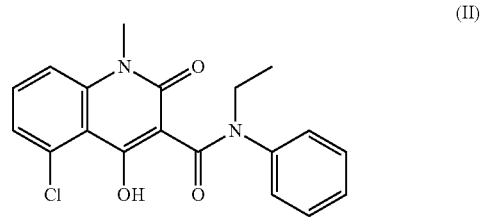 [SMILES: CCN(C(=O)c1c(O)c2c(Cl)cccc2n(C)c1=O)c1ccccc1]

as well as the pharmaceutically acceptable salts, polymorphs, solvates and/or hydrates thereof. Laquinimod as used herein has the IUPAC-name 5-chloro-N-ethyl-4-hydroxy-1-methyl-2-oxo-N-phenyl-1,2-dihydroquinoline-3-carboxamide. In a preferred embodiment of the invention, laquinimod is present in the form of laquinimod free acid or laquinimod salt.

Examples of pharmaceutically acceptable salts of laquinimod include salts with metals such as sodium, potassium, calcium and aluminium. In one embodiment laquinimod is laquinimod sodium.

As used herein, an "amount" or "dose" of siponimod or laquinimod as measured in milligrams refers to the milligrams of siponimod free base or laquinimod free acid present in a preparation, regardless of the form of the preparation. A "dose of 0.6 mg laquinimod" means the amount of laquinimod free acid in a preparation is 0.6 mg, regardless of the form of the preparation. Thus, when in the form of a salt, e.g. laquinimod sodium, the weight of the salt necessary to provide a dose of 0.6 mg laquinimod free acid would be greater than 0.6 mg (e.g., 0.64 mg) due to the presence of the additional salt ion. Similarly, when siponimod is in the form of a salt, e.g. siponimod hemifumarate, the weight of the salt necessary to provide a dose of 0.5 mg siponimod free base would be greater than 0.5 mg due to the presence of the additional salt ion.

As used herein, a "unit dose", "unit doses" and "unit dosage form(s)" mean a single drug administration entity/entities.

As used herein, "about" in the context of a numerical value or range means ±10% of the numerical value or range recited or claimed.

It is understood that where a parameter range is provided, all integers within that range, and tenths thereof, are also provided by the invention. For example, "0.1-2.5 mg/day" includes 0.1 mg/day, 0.2 mg/day, 0.3 mg/day, etc. up to 2.5 mg/day.

Combinations:

The invention relates to a combination comprising siponimod and laquinimod, such as a combined preparation or pharmaceutical composition, for simultaneous, separate or sequential use.

The term "combined preparation" as used herein defines especially a "kit of parts" in the sense, that siponimod and laquinimod can be dosed independently, either in separate form or by use of different fixed combinations with distinguished amounts of the active ingredients. The ratio of the amount of laquinimod to the amount of siponimod to be administered in the combined preparation can be varied, e.g. in order to cope with the needs of a patient sub-population to be treated or the needs of a single patient, which needs can be different due to age, sex, body weight, etc. of a patient. The parts of the kit of parts can be administered simultaneously or chronologically staggered, e.g. at different time points and with equal or different time intervals for any part of the kit of parts.

The combination further may be used as add-on therapy. As used herein, "add-on" or "add-on therapy" means an assemblage of reagents for use in therapy, the subject receiving the therapy begins a first treatment regimen of one or more reagents prior to beginning a second treatment regimen of one or more different reagents in addition to the first treatment regimen, so that not all of the reagents used in the therapy are started at the same time. For example, adding laquinimod therapy to a patient already receiving siponimod therapy.

The administration of the combination comprising siponimod and laquinimod results in a beneficial, for example synergistic, therapeutic effect or in other surprising beneficial effects, for example fewer and/or weaker side effects, compared to a monotherapy applying only one of the active ingredients used in the combination comprising siponimod and laquinimod.

In particular, a combination comprising siponimod and laquinimod, which comprises subeffective doses of siponimod and laquinimod may achieve the same effect as effective doses of either compound alone.

In particular, in patients non-responding to laquinimod, a combination comprising siponimod and laquinimod, may achieve a higher therapeutic effect compared to a monotherapy with siponimod alone.

In particular, in patients non-responding to siponimod, a combination comprising siponimod and laquinimod, may achieve a higher therapeutic effect compared to a monotherapy with laquinimod alone.

A further benefit is that lower doses of siponimod and laquinimod can be used as compared to a monotherapy applying only one of laquinimod or siponimod. For example, the dosages used may not only be smaller, but may also be applied less frequently. Also, the incidence of side effects may be diminished and/or the responder rate to therapies based on laquinimod or siponimod may be higher. All of this is in accordance with the desire and requirements of the patient to be treated.

In one embodiment, the invention provides a combination comprising siponimod and laquinimod, wherein siponimod and laquinimod are present in a therapeutically effective amount.

In one embodiment, the invention provides a combination comprising siponimod and laquinimod, wherein siponimod and laquinimod are present in an amount producing a synergistic therapeutic effect.

In one embodiment, the invention provides a combination comprising siponimod and laquinimod, wherein the amount of laquinimod in the combination is from 0.1 to 10 mg.

In one embodiment, the invention provides a combination comprising siponimod and laquinimod, wherein the amount of laquinimod in the combination is from 0.1 to 2.0 mg.

In one embodiment, the invention provides a combination comprising siponimod and laquinimod, wherein the amount of laquinimod in the combination is from 0.1 to 1.2 mg.

In one embodiment, the invention provides a combination comprising siponimod and laquinimod, wherein the amount of laquinimod in the combination is from 0.1 to 0.5 mg.

In one embodiment, the invention provides a combination comprising siponimod and laquinimod, wherein the amount of laquinimod in the combination is from 0.2 to 0.5 mg.

In one embodiment, the invention provides a combination comprising siponimod and laquinimod, wherein the amount of laquinimod in the combination is 1.2 mg.

In one embodiment, the invention provides a combination comprising siponimod and laquinimod, wherein the amount of laquinimod in the combination is 0.6 mg.

In one embodiment, the invention provides a combination comprising siponimod and laquinimod, wherein the amount of laquinimod in the combination is 0.5 mg.

In one embodiment, the invention provides a combination comprising siponimod and laquinimod, wherein the amount of laquinimod in the combination is 0.3 mg.

In one embodiment, the invention provides a combination comprising siponimod and laquinimod, wherein the amount of laquinimod in the combination is 0.25 mg.

In one embodiment, the invention provides a combination comprising siponimod and laquinimod, wherein laquinimod is laquinimod sodium.

In one embodiment, the invention provides a combination comprising siponimod and laquinimod, wherein the amount of siponimod in the combination is from 0.1 to 10 mg.

In one embodiment, the invention provides a combination comprising siponimod and laquinimod, wherein the amount of siponimod in the combination is from 0.1 to 2.0 mg.

In one embodiment, the invention provides a combination comprising siponimod and laquinimod, wherein the amount of siponimod in the combination is from 0.25 to 1.5 mg.

In one embodiment, the invention provides a combination comprising siponimod and laquinimod, wherein the amount of siponimod in the combination is from 0.5 to 1.5 mg.

In one embodiment, the invention provides a combination comprising siponimod and laquinimod, wherein the amount of siponimod in the combination is 2.0 mg.

In one embodiment, the invention provides a combination comprising siponimod and laquinimod, wherein the amount of siponimod in the combination is 1.5 mg.

In one embodiment, the invention provides a combination comprising siponimod and laquinimod, wherein the amount of siponimod in the combination is 1.0 mg.

In one embodiment, the invention provides a combination comprising siponimod and laquinimod, wherein the amount of siponimod in the combination is 0.5 mg.

In one embodiment, the invention provides a combination comprising siponimod and laquinimod, wherein siponimod is siponimod hemifumarate.

Pharmaceutical Compositions Comprising Siponimod and Laquinimod:

The invention also relates to a pharmaceutical composition comprising siponimod and laquinimod and at least one pharmaceutically acceptable carrier.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

A pharmaceutical composition according to the invention is, preferably, suitable for enteral administration, such as oral or rectal administration; or parenteral administration, such as intramuscular, intravenous, nasal or transdermal administration, to a warm-blooded animal (human beings and animals) that comprises a therapeutically effective amount of the active ingredients and one or more suitable pharmaceutically acceptable carriers.

Preferred are compositions for oral administration.

A composition for enteral or parenteral administration is, for example, a unit dosage form, such as a tablet, a capsule, a suppository or an ampoule.

The unit content of active ingredients in an individual dose need not in itself constitute a therapeutically effective amount, since such an amount can be reached by the administration of a plurality of dosage units. A composition according to the invention may contain, e.g., from about 10% to about 100% of the therapeutically effective amount of the active ingredients.

In one embodiment, the invention provides a composition comprising siponimod and laquinimod and at least one pharmaceutically acceptable carrier, wherein the amount of laquinimod in the composition is from 0.1 to 10 mg.

In one embodiment, the invention provides a composition comprising siponimod and laquinimod and at least one pharmaceutically acceptable carrier, wherein the amount of laquinimod in the composition is from 0.1 to 2.0 mg.

In one embodiment, the invention provides a composition comprising siponimod and laquinimod and at least one pharmaceutically acceptable carrier, wherein the amount of laquinimod in the composition is from 0.1 to 1.2 mg.

In one embodiment, the invention provides a composition comprising siponimod and laquinimod and at least one pharmaceutically acceptable carrier, wherein the amount of laquinimod in the composition is from 0.1 to 0.5 mg.

In one embodiment, the invention provides a composition comprising siponimod and laquinimod and at least one pharmaceutically acceptable carrier, wherein the amount of laquinimod in the composition is from 0.2 to 0.5 mg.

In one embodiment, the invention provides a composition comprising siponimod and laquinimod and at least one pharmaceutically acceptable carrier, wherein the amount of laquinimod in the composition is 1.2 mg.

In one embodiment, the invention provides a composition comprising siponimod and laquinimod and at least one pharmaceutically acceptable carrier, wherein the amount of laquinimod in the composition is 0.6 mg.

In one embodiment, the invention provides a composition comprising siponimod and laquinimod and at least one pharmaceutically acceptable carrier, wherein the amount of laquinimod in the composition is 0.5 mg.

In one embodiment, the invention provides a composition comprising siponimod and laquinimod and at least one pharmaceutically acceptable carrier, wherein the amount of laquinimod in the composition is 0.3 mg.

In one embodiment, the invention provides a composition comprising siponimod and laquinimod and at least one pharmaceutically acceptable carrier, wherein the amount of laquinimod in the composition is 0.25 mg.

In one embodiment, the invention provides a composition comprising siponimod and laquinimod and at least one pharmaceutically acceptable carrier, wherein laquinimod is laquinimod sodium.

In one embodiment, the invention provides a composition comprising siponimod and laquinimod and at least one pharmaceutically acceptable carrier, wherein the amount of siponimod in the composition is from 0.1 to 10 mg.

In one embodiment, the invention provides a composition comprising siponimod and laquinimod and at least one pharmaceutically acceptable carrier, wherein the amount of siponimod in the composition is from 0.1 to 2.0 mg.

In one embodiment, the invention provides a composition comprising siponimod and laquinimod and at least one pharmaceutically acceptable carrier, wherein the amount of siponimod in the composition is from 0.25 to 1.5 mg.

In one embodiment, the invention provides a composition comprising siponimod and laquinimod and at least one pharmaceutically acceptable carrier, wherein the amount of siponimod in the composition is from 0.5 to 1.5 mg.

In one embodiment, the invention provides a composition comprising siponimod and laquinimod and at least one pharmaceutically acceptable carrier, wherein the amount of siponimod in the composition is 2.0 mg.

In one embodiment, the invention provides a composition comprising siponimod and laquinimod and at least one pharmaceutically acceptable carrier, wherein the amount of siponimod in the composition is 1.5 mg.

In one embodiment, the invention provides a composition comprising siponimod and laquinimod and at least one pharmaceutically acceptable carrier, wherein the amount of siponimod in the composition is 1.0 mg.

In one embodiment, the invention provides a composition comprising siponimod and laquinimod and at least one pharmaceutically acceptable carrier, wherein the amount of siponimod in the composition is 0.5 mg.

In one embodiment, the invention provides a composition comprising siponimod and laquinimod and at least one pharmaceutically acceptable carrier, wherein siponimod is siponimod hemifumarate.

If not indicated otherwise, a pharmaceutical composition according to the invention is pre-pared in a manner known per se, e.g. by means of conventional mixing, granulating, coating, dissolving or lyophilizing processes. In preparing a composition for an oral dosage form, any of the usual pharmaceutical media may be employed, for example water, glycols, oils, alcohols, carriers, such as starches, sugars, or microcrystalline cellulose, diluents, granulating agents, lubricants, binders, disintegrating agents and the like. Because of their ease of administration, tablets and capsules represent the most advantageous oral dosage unit forms, in which case solid pharmaceutical carriers are obviously employed.

In one embodiment, the invention provides a pharmaceutical composition comprising siponimod and laquinimod and at least one pharmaceutically acceptable carrier, wherein the composition is a tablet or capsule.

In one embodiment, the invention provides a pharmaceutical composition comprising siponimod and laquinimod and at least one pharmaceutically acceptable carrier, wherein the composition is a tablet.

In one embodiment, the invention provides a pharmaceutical composition comprising siponimod and laquinimod and at least one pharmaceutically acceptable carrier, wherein the composition is a capsule.

Using Combinations Comprising Siponimod and Laquinimod to Treat Autoimmune Diseases, e.g. SPMS:

Surprisingly it was found that combinations comprising siponimod and laquinimod are effective to improve disease burden and synergistically reduce the number of lymphocytes in a curative EAE model, i.e. administration to C57/Bl6 mice after EAE was induced by MOG/CFA/*Pertussis* toxin injection and clinical symptoms became manifest. As this model is a model for MS treatments administered to a damaged CNS (e.g. after disease outbreak/a relapse occurred), this model is especially relevant for later stage RRMS patients or SPMS patients and not for relapse prevention in a clinically normal patient. Consequently, compared to therapies using siponimod alone, combinations comprising siponimod and laquinimod may be able to lessen inflammatory events, e.g. inflammation in the meninges, in the CNS of SPMS patients and/or (ii) effectively reduce the number and/or severity of relapses in SPMS patients.

The combinations comprising siponimod and laquinimod can be used in the treatment of an autoimmune disease, such as multiple sclerosis (MS), for example relapsing-remitting MS (RRMS), primary progressive MS (PPMS), secondary progressive MS (SPMS) and relapsing SPMS. The siponimod of the present invention is preferably used for the treatment of RRMS and/or SPMS, most preferably SPMS.

"SPMS" is defined as "initial relapsing remitting disease course followed by progression with or without occasional relapses, minor remissions, and plateaus" (Lublin, F. D., Reingold, S. C. (1996) Defining the clinical course of multiple sclerosis. Neurology, 46: 907-911). The diagnosis of MS with initial relapsing remitting disease course is defined by the 2010 Revised McDonald criteria (Polman C H, Reingold S, Banwell B, et al. (2011). Diagnostic criteria for multiple sclerosis: 2010 revisions to the McDonald criteria. Ann Neurol; 68: 292-302). Progression denotes the continuous worsening of neurological impairment over at last 6 months (Rovaris M., Confavreux C., Furlan R. et al. (2006). Secondary progressive multiple sclerosis: current knowledge and future challenges; Lancet Neurology 5: 343-354) not explained by incomplete recovery from relapses (Lublin, F. D., Baier, M., Cutter, G. (2003) Effect of relapses on development on residual deficit in multiple sclerosis. Neurology, 51: 1528-1532).

In one embodiment, combinations comprising siponimod and laquinimod are used for the treatment of SPMS patients characterized by a progressive increase in disability of at least 6 months' duration in the absence of relapses or independent of relapses.

In one embodiment, combinations comprising siponimod and laquinimod are used for the treatment of SPMS patients having a disability status with an EDSS score of 2.0 to 8.0, more preferably 2.5 to 7.0, most preferably 3.0 to 6.5.

"EDSS" stands for the Kurtzke Expanded Disability Status Scale, which is a method of quantifying disability in multiple sclerosis (cf. Table 1). The EDSS quantifies disability in eight Functional Systems (FS) and allows neurologists to assign a Functional System Score (FSS) in each of these. Kurtzke defines functional systems as follows: pyramidal, cerebellar, brainstem, sensory, bowel and bladder, visual, cerebral, other.

The Functional Systems (FS) are scored on a scale of 0 (low level of problems) to 5 (high level of problems) to best reflect the level of disability observed clinically. The "Other" category is not rated numerically, but measures disability related to a particular issue, like motor loss.

In contrast, the total EDSS score is determined by two factors: gait and FS scores. EDSS scores below 4.0 are determined by the FS scores alone. People with EDSS scores of 4.0 and above have some degree of gait impairment. Scores between 4.0 and 9.5 are determined by both gait abilities and the FS scores.

TABLE 1

Kurtzke Expanded Disability Status Scale

| | |
|---|---|
| 0 | Normal neurological exam (all grade 0 in Functional Systems (FS); cerebral grade 1 acceptable). |
| 1 | No disability, minimal signs in one FS (i.e. one grade 1 excluding cerebral grade 1). |
| 1.5 | No disability, minimal signs in more than one FS (more than one grade 1 excluding cerebral grade 1). |
| 2.0 | Minimal disability in one FS (one FS grade 2, others 0 or 1). |
| 2.5 | Minimal disability in two FS (two FS grade 2, others 0 or 1). |
| 3.0 | Moderate disability in one FS (one FS grade 3, others 0 or 1), or mild disability in three or four FS (three-four FS grade 2, others 0 or 1). |
| 3.5 | Fully ambulatory but with moderate disability in one FS (one grade 3 and one or two FS grade 2) or two FS grade 3, others 0 or 1, or five FS grade 2, others 0 or 1. |
| 4.0 | Fully ambulatory without aid, self-sufficient, up and about some 12 hours a day despite relatively severe disability consisting of one FS grade 4 (others 0 or 1), or combinations of lesser grades exceeding limits of previous steps. Able to walk without aid or rest some 500 meters (0.3 miles). |
| 4.5 | Fully ambulatory without aid, up and about much of the day, able to work a full day, may otherwise have some limitation of full activity or require minimal assistance; characterized by relatively severe disability. (Usually consisting of one FS grade 4 (others 0 or 1) or combinations of lesser grades exceeding limits of previous steps. Able to walk without aid or rest for some 300 meters (975 ft.).) |
| 5.0 | Ambulatory without aid or rest for about 200 meters (650 ft.); disability severe enough to impair full daily activities (e.g. to work full day without special provisions). (Usual FS equivalents are one grade 5 alone (others 0 or 1); or combinations of lesser grades usually exceeding specifications for step 4.0.) |
| 5.5 | Ambulatory without aid or rest for about 100 meters (325 ft); disability severe enough to impair full daily activities. (Usual FS equivalents are one grade 5 alone (others 0 or 1); or combinations of lesser grades usually exceeding specifications for step 4.0.) |
| 6.0 | Intermittent or constant unilateral assistance (cane, crutch or brace) required to walk about 100 meters (325 ft.) with or without resting. (Usual FS equivalents are combinations with more than two FS grade 3+.) |
| 6.5 | Constant bilateral assistance (canes, crutches or braces) required to walk about 20 meters (65 ft.). (Usual FS equivalents are combinations with more than two FS grade 3+.) |
| 7.0 | Unable to walk beyond about 5 meters (16 ft.) event with aid, essentially restricted to wheelchair, wheels self in standard wheelchair a full day and transfers alone; up and about in wheelchair some 12 hours a day. (Usual FS equivalents are combinations with more than one FS grade 4+; very rarely pyramidal grade 5 alone.) |
| 7.5 | Unable to take more than a few steps; restricted to wheelchair; may need aid in transfers, wheels self but cannot carry on in standard wheelchair a full day; may require motorized wheelchair. (Usual FS equivalents are combinations with more than one FS grade 4+.) |

TABLE 1-continued

Kurtzke Expanded Disability Status Scale 8.0 Essentially restricted to bed or chair or perambulated in wheelchair; but may be out of bed much of the day; retains many self-care functions; generally has effective use of arms. (Usual FS equivalents are combinations, generally grade 4+ in several systems.)

8.5 Essentially restricted to bed for much of the day; has some effective use of arm(s); retains some self-care functions. (Usual FS equivalents are combinations, generally grade 4+ in several systems.)

9.0 Helpless bed patient; can communicate and eat. (Usual FS equivalents are combinations, mostly grade 4.)

9.5 Totally helpless bed patient; unable to communicate or effectively eat/swallow. (Usual FS equivalents are combinations, almost all grade 4+.)

10 Death due to MS.

The terms "treatment"/"treating" as used herein includes: (1) preventing or delaying the appearance of clinical symptoms of the state, disorder or condition developing in an animal, particularly a mammal and especially a human, that may be afflicted with or predisposed to the state, disorder or condition but does not yet experience or display clinical or subclinical symptoms of the state, disorder or condition; (2) inhibiting the state, disorder or condition (e.g. arresting, reducing or delaying the development of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

In one embodiment, the combinations comprising siponimod and laquinimod are effective to reduce a symptom of RRMS or SPMS, preferably SPMS. In one embodiment, the symptom is an MRI-monitored multiple sclerosis disease activity, disability progression, brain atrophy, neuronal dysfunction, neuronal injury, neuronal degeneration, deterioration of visual function, impaired mobility, cognitive impairment, reduction of brain volume, deterioration in general health status, functional status and/or quality of life.

In one embodiment, the combinations comprising siponimod and laquinimod, in patients with SPMS, delay disability progression, e.g. as assessed by EDSS.

In one embodiment, the treatment comprises increasing the time to 3-month confirmed disability progression in patients with SPMS as measured by EDSS compared to untreated patients. Disability progression as measured by EDSS typically is defined as an increase from the baseline of at least 1 point (in patients with a baseline EDSS score of 3.0 to 5.0) or of at least 0.5 point (in patients with a baseline EDSS score of 5.5. to 6.5). To confirm that the progression is sustained, this increase must be present at a visit 3 months later.

In one embodiment, time to 3-month confirmed disability progression is increased by at least 10%.

In one embodiment, time to 3-month confirmed disability progression is increased by at least 25%.

In one embodiment, time to 3-month confirmed disability progression is increased by 20 to 75%.

In one embodiment, time to 3-month confirmed disability progression is increased by 10 to 75%.

In another embodiment, time to 3-month confirmed disability progression is increased by 25 to 50%.

In another embodiment, time to 3-month confirmed disability progression is increased by 25 to 40%.

In one embodiment, the combinations comprising siponimod and laquinimod of the present invention, in patients with SPMS, delay worsening of impaired mobility, e.g. as assessed by the timed 25-foot walk test (T25-FW).

The T25-FW is a quantitative mobility and leg function performance test based on a timed 25-walk. The patient is directed to one end of a clearly marked 25-foot course and is instructed to walk 25 feet as quickly as possible, but safely. The time is calculated from the initiation of the instruction to start and ends when the patient has reached the 25-foot mark. The task is immediately repeated again by having the patient walk back the same distance. The T25-FW is one of three components of the Multiple Sclerosis Functional Composite (MSFC), a composite measure assessing upper extremity function, ambulation and cognitive function (Fisher J S et al. for the National MS Society Clinical Outcomes Assessment Task Force (1999). The multiple sclerosis functional composite measure: an integrated approach to MS clinical outcome assessment. Mult Scler; 5: 244-250).

In one embodiment, treatment comprises delaying the time to 3-month confirmed worsening of at least 20% from the baseline in the T25-FW compared to untreated patients.

In one embodiment, time to 3-month confirmed worsening of at least 20% from the baseline in the T25-FW compared to untreated patients is increased by at least 10%.

In one embodiment, time to 3-month confirmed worsening of at least 20% from the baseline in the T25-FW compared to untreated patients is increased by at least 25%.

In one embodiment, time to 3-month confirmed worsening of at least 20% from the baseline in the T25-FW compared to untreated patients is increased by 10 to 80%.

In one embodiment, time to 3-month confirmed worsening of at least 20% from the baseline in the T25-FW compared to untreated patients is increased by 20 to 80%.

In another embodiment, time to 3-month confirmed worsening of at least 20% from the baseline in the T25-FW compared to untreated patients is increased by 25 to 70%.

In another embodiment, time to 3-month confirmed worsening of at least 20% from the baseline in the T25-FW compared to untreated patients is increased by 25 to 50%.

In one embodiment, the combinations comprising siponimod and laquinimod, in patients with SPMS, reduce the increase in T2 lesion volume, e.g. increase within 2 years of treatment from the baseline compared to untreated patients, as measured by Magnetic Resonance Imaging (MRI). T2 lesions are detected using MR-images that emphasize T2 contrast. T2 lesions represent new inflammatory activity.

In one embodiment, increase in T2 lesion volume within 2 years of treatment from the baseline is reduced compared to untreated patients by at least 10%.

In one embodiment, increase in T2 lesion volume within 2 years of treatment from the baseline is reduced compared to untreated patients by at least 25%.

In one embodiment, increase in T2 lesion volume within 2 years of treatment from the baseline is reduced compared to untreated patients by 10 to 100%.

In one embodiment, increase in T2 lesion volume within 2 years of treatment from the baseline is reduced compared to untreated patients by 20 to 100%.

In another embodiment, increase in T2 lesion volume within 2 years of treatment from the baseline is reduced compared to untreated patients by 25 to 90%.

In another embodiment, increase in T2 lesion volume within 2 years of treatment from the baseline is reduced compared to untreated patients by 30 to 80%.

In one embodiment, the combinations comprising siponimod and laquinimod decrease or inhibit reduction of brain volume in patients with SPMS, measured by percent brain volume change.

In one embodiment, the combinations comprising siponimod and laquinimod, in patients with SPMS, increase a general health status or delay a deterioration of the general health status, as defined by the EQ-5D. EQ-5D is a standardized questionnaire used for measuring the general health status. It measures five domains (mobility, self-care, usual activity, pain/discomfort, anxiety/depression).

In one embodiment, the combinations comprising siponimod and laquinimod, in patients with SPMS, increase or delay a reduction of the health-related quality of life as measured by the Multiple Sclerosis Impact Scale (MSIS-29), an instrument measuring the physical (20 items) and psychological (nine items) impact of multiple sclerosis.

In one embodiment, the combinations comprising siponimod and laquinimod, in patients with SPMS, reduce the annualized relapse rate. The term "relapse rate" as used herein refers to the number of confirmed relapses per unit time. The term "annualized relapse rate" as used herein refers to the mean value of the number of confirmed relapses of each patient multiplied by 365 and divided by the number of days that patient is on the drug.

The term "subject" as used herein refers preferably to a human being, especially to a patient being diagnosed with MS, e.g. SPMS.

The term "therapeutically effective amount" as used herein typically refers to an amount of an active ingredient or of a combination of active ingredients which, when administered to a subject, is sufficient to provide a therapeutic benefit, e.g. is sufficient for treating, preventing or delaying the progression of SPMS (e.g. the amount provides an amelioration of symptoms).

For the above-mentioned indications (the conditions and disorders) the appropriate dosage of active ingredients will vary depending upon, for example, the solid form of the compound employed, the host, the mode of administration and the nature and severity of the condition being treated.

In humans, an indicated daily dosage for laquinimod is in the range from about 0.1 to about 10 mg, e.g. from about 0.1 to about 2.0 mg or from about 0.1 to about 1.2 mg of laquinimod conveniently administered, for example, in divided doses up to four times a day (e.g. four times administration per day of the same unit dosage form of the combination comprising siponimod and laquinimod).

In humans, an indicated daily dosage for siponimod is in the range from about 0.1 to about 10 mg, e.g. from about 0.1 to about 2.0 mg or from about 0.25 to about 1.5 mg of siponimod conveniently administered, for example, in divided doses up to four times a day (e.g. four times administration per day of the same unit dosage form of the combination comprising siponimod and laquinimod).

A physician or clinician of ordinary skill can readily determine and prescribe the appropriate dosage regimen.

Unit dosage forms of laquinimod may contain 0.1-10 mg laquinimod p.o.

Unit dosage forms of siponimod may contain 0.1-10 mg siponimod p.o.

The usefulness of the combination comprising siponimod and laquinimod in the treatment of the above-mentioned disorders, e.g. SPMS, can be confirmed in a range of standard tests including those indicated below.

EXAMPLES

Example 1

Data from Animal Models

Example 1.1

Level of Siponimod in Cerebrospinal Fluid (CSF) in Mice

Female C57Bl/6 mice were treated daily with 3 mg/kg siponimod, p.o. for 8 days. 8 hours after the last administration, animals were sacrificed and the levels of siponimod were measured in blood, brain and CSF.

Data is summarized in Table 1 below. Shown are mean values of 3-5 animals and standard error of the mean (in brackets).

TABLE 1

| Strain and species | Dose (mg/kg, qd) | sampling day | time | conc siponimod (nM) (SEM) | | |
|---|---|---|---|---|---|---|
| | | | | Blood | Brain | CSF |
| C57Bl/6 mice | 3 | 8 | 8 h | 973.3 (62.1) | 5552 (298) | 7.2 (1) |
| C57Bl/6 mice, EAE | 3 | 8 | 8 h | 1600 (79) | 9193 (310) | 17.7 (3.2) |

This shows that a clinically relevant dose of siponimod (3 mg/kg in mice) leads to exposures in the CSF above the $EC_{50}$ for S1P1 (0.4 nM) and S1P5 (1 nM).

Example 1.2

Use of Siponimod, Laquinimod and Combinations Thereof to Reduce Lymphocytes in MOG/CFA/*Pertussis* Toxin-Treated C57/Bl6 Mice Female C57Bl/6 mice were subcutaneously immunized with 200 μg recombinant MOG1-125 in CFA followed by one i.p. injection of 100 ng *Pertussis* toxin. Two days later an additional i.p. injection of 100 ng *pertussis* toxin was administered. Three days after the first clinical symptoms, the mice were randomized to either vehicle, 0.3 mg/kg siponimod, 10 mg/kg laquinimod or 0.3 mg/kg siponimod+ 10 mg/kg laquinimod and treated daily with said doses for 29 days. The MOG/CFA/*Pertussis* toxin-induced experimental autoimmune encephalomyelitis model in C57/Bl6 mice is described in Quancard et al (Chem Biol. 19(9):1142-51, 2012).

Results are shown in FIG. 1. Treatment with 10 mg/kg laquinimod did not significantly reduce lymphocytes. Treatment with 0.3 mg/kg siponimod reduced lymphocytes. A combination of 0.3 mg/kg siponimod+10 mg/kg laquinimod demonstrated a synergistic effect on lymphocyte reduction. Statistical significance p<0.05.

Example 1.2

Use of Siponimod, Laquinimod and Combinations Thereof to Treat MOG/CFA/*Pertussis* Toxin-Immunized Experimental Autoimmune Encephalomyelitis (EAE) in C57/Bl6 Mice Female C57Bl/6 mice were subcutaneously immunized with 200 μg recombinant MOG1-125 in CFA followed by one i.p. injection of 100 ng *Pertussis* toxin. Two days later an additional i.p. injection of 100 ng *pertussis* toxin was administered. Three days after the first clinical symptoms, the mice were randomized to either vehicle, 0.3 mg/kg siponimod, 10 mg/kg laquinimod or 0.3 mg/kg siponimod+ 10 mg/kg laquinimod and treated daily with said doses for 30 days. Treatment initiated after severe CNSneurological disease and tissue damage has occurred. More specifically after that a severe CNS damage, which can be characterized by hind limb paralysis, had already occurred.

Figure 2:
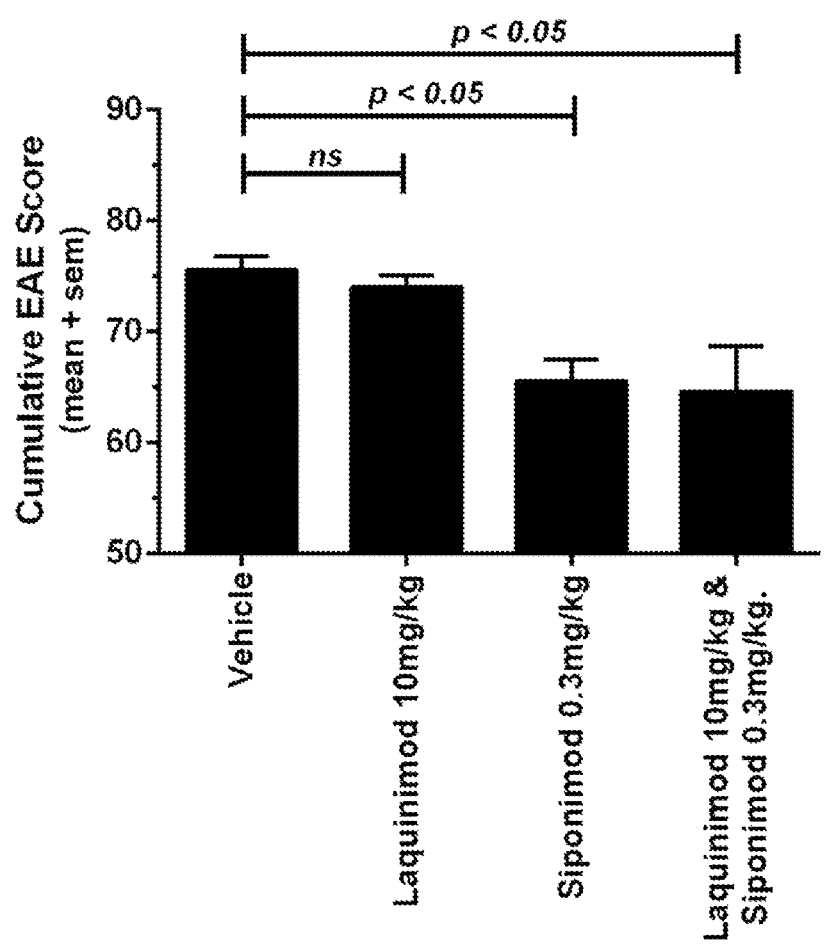
FIG. 2: Use of siponimod and laquinimod to treat MOG/CFA/*Pertussis* toxin-induced experimental autoimmune encephalomyelitis (EAE) in C57/Bl6 mice. Treatment initiated after severe CNS damage, which, for instance, is characterized by hind limb paralysis.

Results are shown in FIG. 2. Treatment with 10 mg/kg laquinimod did not significantly improve disease burden (cumulative EAE score). Treatment with 0.3 mg/kg siponimod reduced disease burden (cumulative EAE score). A combination of 0.3 mg/kg siponimod+10 mg/kg laquinimod demonstrated a significantly improve disease burden (cumulative EAE score) compared to vehicle-treated animals. Statistical significance p<0.05.

Example 1.3

Level of Siponimod and Laquinimod in Blood and Brain Tissue Durinq Experimental Autoimmune Encephalomyelitis (EAE) in C57/Bl6 Mice Female C57Bl/6 mice were subcutaneously immunized with 200 μg recombinant MOG1-125 in CFA followed by one i.p. injection of 100 ng *Pertussis* toxin. Two days later an additional i.p. injection of 100 ng *pertussis* toxin was administered. Mice were dosed with either vehicle, 0.3 mg/kg siponimod, 10 mg/kg laquinimod or 0.3 mg/kg siponimod+10 mg/kg laquinimod for up to 21 days. Treatment initiated after immune cells have entered the CNS resulting in paralysis and localised tissue damage.

Figure 3:
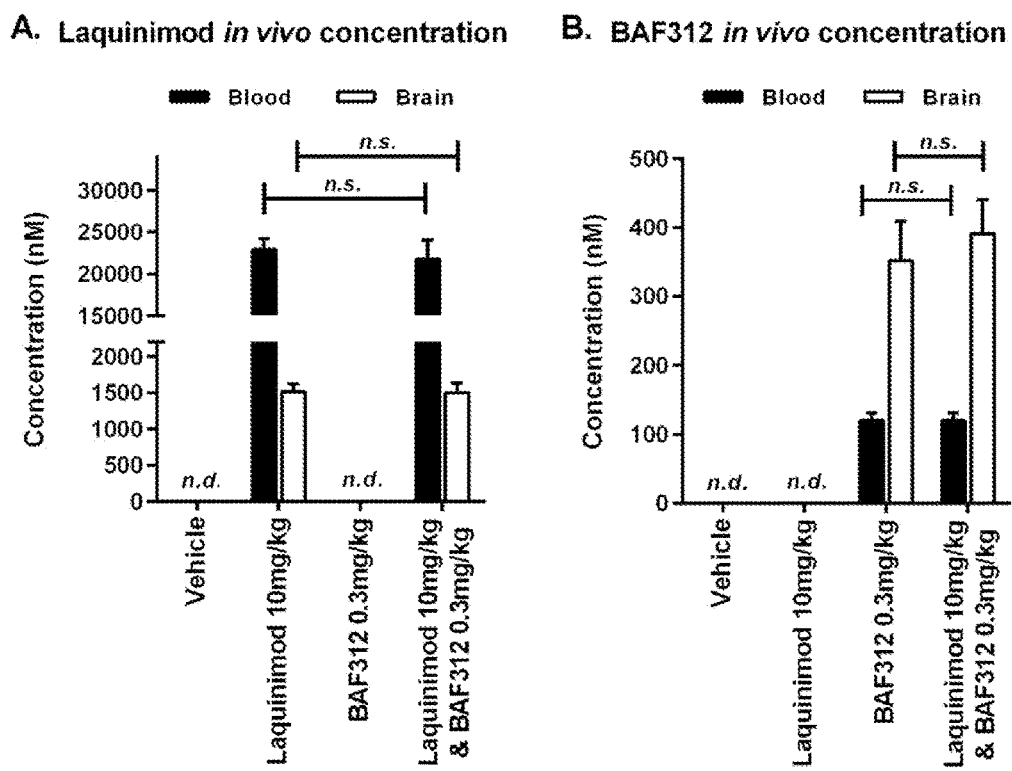
FIG. 3: Level of siponimod and laquinimod in blood and brain tissue during experimental autoimmune encephalomyelitis (EAE) in C57/Bl6 mice. No evidence of drug-drug interactions.

Results are shown in FIG. 3. Combination therapy did not significantly alter either the blood or brain concentration of siponimod or laquinimod. There was no evidence of drug-drug interactions. The efficacy of combination therapy represents an enhanced biological response. No statistical significance p>0.05.

Example 1.4

Use of Siponimod, Laquinimod and Combinations Thereof to Treat MOG/CFA/*Pertussis* Toxin-Immunized Experimental Autoimmune Encephalomyelitis (EAE) in C57/Bl6 Mice Female C57Bl/6 mice were subcutaneously immunized with 200 μg recombinant MOG1-125 in CFA followed by one i.p. injection of 100 ng *Pertussis* toxin. Two days later an additional i.p. injection of 100 ng *pertussis* toxin was administered. Following infiltration of immune cells into the CNS to initiate tissue damage, the mice were randomized to either vehicle, 0.3 mg/kg siponimod, 10 mg/kg laquinimod or 0.3 mg/kg siponimod+10 mg/kg laquinimod and treated daily with said doses for 21 days.

Figure 4:
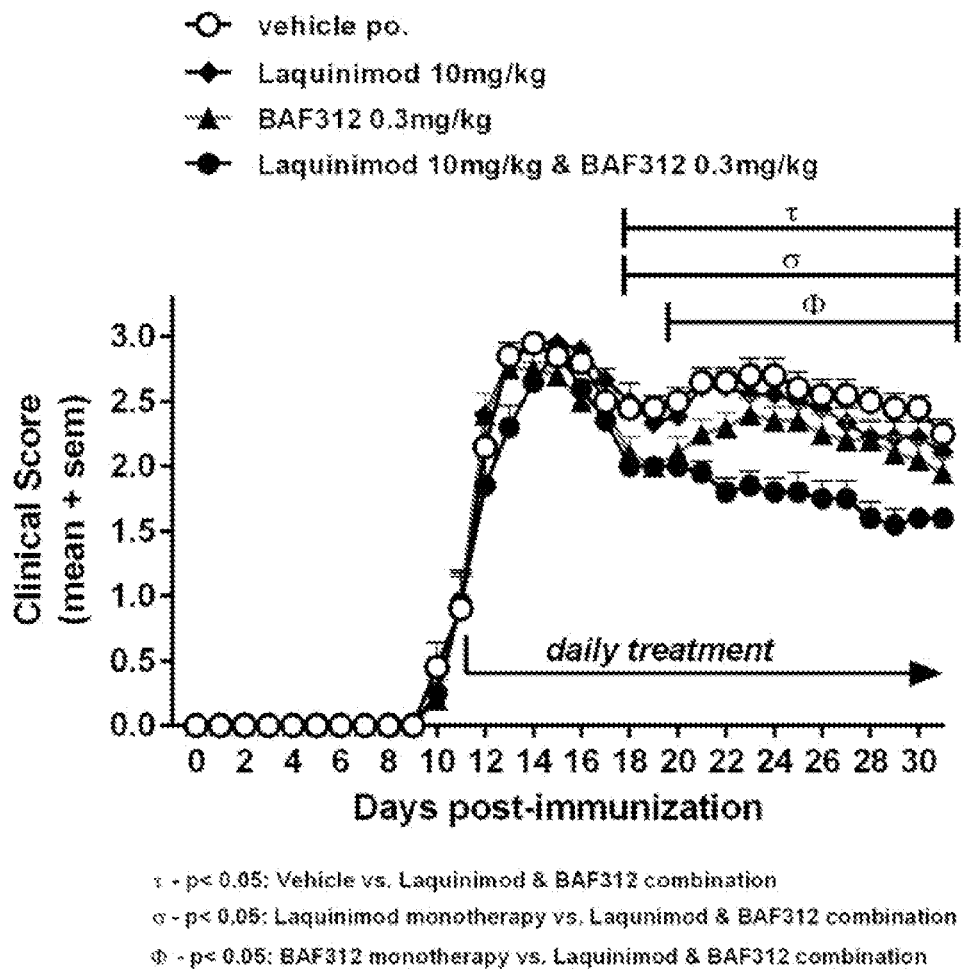
FIG. 4: Use of siponimod and laquinimod to treat MOG/CFA/*Pertussis* toxin-induced experimental autoimmune encephalomyelitis (EAE) in C57/Bl6 mice. Treatment initiated during ongoing CNS damage (e.g. after disease outbreak).

Results are shown in FIG. 4. Treatment with 10 mg/kg laquinimod did not significantly improve daily disease severity. Treatment with 0.3 mg/kg siponimod transiently reduced neurological paralysis (days post-immunization 18-21), however, animals ultimately entered the chronic non-remitting phase. A combination of 0.3 mg/kg siponimod+10 mg/kg laquinimod demonstrated a significantly improve disease burden compared to vehicle-treated animals. The recovery from neurological paralysis was significantly greater than either laquinimod or siponimod monotherapy. Statistical significance p<0.05.

Example 2

Clinical Study

A multicentre, randomized, double-blind, parallel-group, placebo-controlled variable treatment duration study evaluating the efficacy and safety of a combination of siponimod and laquinimod in patients with Secondary Progressive Multiple Sclerosis.

1. Study Objectives
a) Primary Objective

The primary objective is to demonstrate the efficacy of a combination of siponimod and laquinimod relative to placebo in delaying the time to 3-month confirmed disability progression in patients with SPMS as measured by EDSS.

b) Key Secondary Objectives

The first key secondary objective is to demonstrate the efficacy of a combination of siponimod and laquinimod relative to placebo in delaying the time to 3-month confirmed worsening of at least 20% from the baseline in the timed 25-foot walk test (T25-FW).

The second key secondary objective is to demonstrate the efficacy of a combination of siponimod and laquinimod relative to placebo in reducing the increase in T2 lesion volume from the baseline to the end of the study.

c) Further Secondary Objectives Include

To evaluate the efficacy of a combination of siponimod and laquinimod relative to placebo in delaying the time to 6-month confirmed disability progression as measured by EDSS To evaluate the efficacy of a combination of siponimod and laquinimod relative to placebo in reducing the frequency of confirmed relapses as evaluated by the annualized relapse rate (ARR), and to evaluate time to first relapse and proportion of relapse-free patients To evaluate the effect of a combination of siponimod and laquinimod compared to placebo on the patient reported outcome Multiple Sclerosis Walking Scale (MSWS-12)

To evaluate the efficacy of a combination of siponimod and laquinimod compared to placebo with respect to inflammatory disease activity and burden of disease, as measured by conventional MRI (T1 Gd-enhancing lesions, new or enlarging T2 lesions, brain volume)

To evaluate the safety and tolerability of a combination of siponimod and laquinimod vs. placebo d) Exploratory Objectives Include To evaluate the effect of a combination of siponimod and laquinimod compared to placebo on the following patient-reported outcomes:

The health-related quality of life (QoL) as measured by the Multiple Sclerosis Impact Scale (MSIS-29)

The health-related quality of life (QoL) as measured by the EQ-5D

To explore efficacy of a combination of siponimod and laquinimod relative to placebo on defined cognitive tests:

Paced Auditory Serial Addition Test (PASAT)

Symbol Digit Modalities Test (SDMT)

Brief Visuospatial Memory Test Revised (BVMTR)

To evaluate the efficacy of a combination of siponimod and laquinimod relative to placebo in the evolution of acute lesions into chronic black holes by MRI To evaluate the efficacy of a combination of siponimod and laquinimod relative to placebo on the MSFC z-score To evaluate the efficacy of a combination of siponimod and laquinimod relative to placebo in delaying the time to:

3-month confirmed worsening of at least 20% from the baseline in the timed 25-foot walk test (T25W) or 3-month confirmed disability progression as measured by EDSS score or 3-month confirmed worsening of at least 20% from the baseline in the 9-hole peg test (9-HPT) in either one of the hands (dominant or non-dominant).

To explore the relationship between disability progression endpoints and drug concentrations/lymphocyte count To explore the relationship between selected safety parameters and drug concentrations/lymphocyte count To evaluate the pharmacokinetics of siponimod and laquinimod 2. Population The study population consists of ambulatory patients with an EDSS score of 3.0 to 6.5 and aged between 18 to 60 years with a diagnosis of MS with a secondary progressive disease course (SPMS).

3. Study Design

This is a randomized, multicenter, double-blind, placebo-controlled parallel-group study in patients with SPMS. Patients are randomized to receive either a combination of siponimod and laquinimod or placebo.

The following are further embodiments of the invention:

Embodiment 1: A combination comprising siponimod and laquinimod for use in the treatment, prevention or delay of progression of secondary progressive multiple sclerosis.

Embodiment 1.1: A combination according to embodiment 1, wherein the amount of laquinimod in the combination is from 0.1 to 10 mg.

Embodiment 1.2: A combination according to embodiment 1, wherein the amount of laquinimod in the combination is from 0.1 to 2.0 mg.

Embodiment 1.3: A combination according to embodiment 1, wherein the amount of laquinimod in the combination is from 0.1 to 1.2 mg.

Embodiment 1.4: A combination according to embodiment 1, wherein the amount of laquinimod in the combination is from 0.1 to 0.5 mg.

Embodiment 1.5: A combination according to embodiment 1, wherein the amount of laquinimod in the combination is from 0.2 to 0.5 mg.

Embodiment 1.6: A combination according to embodiment 1, wherein the amount of laquinimod in the combination is 1.2 mg.

Embodiment 1.7: A combination according to embodiment 1, wherein the amount of laquinimod in the combination is 0.6 mg.

Embodiment 1.8: A combination according to embodiment 1, wherein the amount of laquinimod in the combination is 0.5 mg.

Embodiment 1.9: A combination according to embodiment 1, wherein the amount of laquinimod in the combination is 0.3 mg.

Embodiment 1.10: A combination according to embodiment 1, wherein the amount of laquinimod in the combination is 0.25 mg.

Embodiment 1.11: A combination according to any of embodiments 1 to 1.10, wherein laquinimod is laquinimod sodium.

Embodiment 1.12: A combination according to any of embodiments 1 to 1.11, wherein the amount of siponimod in the combination is from 0.1 to 10 mg.

Embodiment 1.13: A combination according to any of embodiments 1 to 1.11, wherein the amount of siponimod in the combination is from 0.1 to 2.0 mg.

Embodiment 1.14: A combination according to any of embodiments 1 to 1.11, wherein the amount of siponimod in the combination is from 0.25 to 1.5 mg.

Embodiment 1.15: A combination according to any of embodiments 1 to 1.11, wherein the amount of siponimod in the combination is from 0.5 to 1.0 mg.

Embodiment 1.16: A combination according to any of embodiments 1 to 1.11, wherein the amount of siponimod in the combination is 2.0 mg.

Embodiment 1.17: A combination according to any of embodiments 1 to 1.11, wherein the amount of siponimod in the combination is 1.5 mg.

Embodiment 1.18: A combination according to any of embodiments 1 to 1.11, wherein the amount of siponimod in the combination is 1.0 mg.

Embodiment 1.19: A combination according to any of embodiments 1 to 1.11, wherein the amount of siponimod in the combination is 0.5 mg.

Embodiment 1.20: A combination according to any of embodiments 1 to 1.19, wherein siponimod is siponimod hemifumarate.

Embodiment 2: A combination comprising siponimod and laquinimod for the use as a medicament.

Embodiment 2.1: A combination according to embodiment 2, wherein the amount of laquinimod in the combination is from 0.1 to 10 mg.

Embodiment 2.2: A combination according to embodiment 2, wherein the amount of laquinimod in the combination is from 0.1 to 2.0 mg.

Embodiment 2.3: A combination according to embodiment 2, wherein the amount of laquinimod in the combination is from 0.1 to 1.2 mg.

Embodiment 2.4: A combination according to embodiment 2, wherein the amount of laquinimod in the combination is from 0.1 to 0.5 mg.

Embodiment 2.5: A combination according to embodiment 2, wherein the amount of laquinimod in the combination is from 0.2 to 0.5 mg.

Embodiment 2.6: A combination according to embodiment 2, wherein the amount of laquinimod in the combination is 1.2 mg.

Embodiment 2.7: A combination according to embodiment 2, wherein the amount of laquinimod in the combination is 0.6 mg.

Embodiment 2.8: A combination according to embodiment 2, wherein the amount of laquinimod in the combination is 0.5 mg.

Embodiment 2.9: A combination according to embodiment 2, wherein the amount of laquinimod in the combination is s 0.3 mg.

Embodiment 2.10: A combination according to embodiment 2, wherein the amount of laquinimod in the combination is 0.25 mg.

Embodiment 2.11: A combination according to any of embodiments 2 to 2.10, wherein laquinimod is laquinimod sodium.

Embodiment 2.12: A combination according to any of embodiments 2 to 2.11, wherein the amount of siponimod in the combination is from 0.1 to 10 mg.

Embodiment 2.13: A combination according to any of embodiments 2 to 2.11, wherein the amount of siponimod in the combination is from 0.1 to 2.0 mg.

Embodiment 2.14: A combination according to any of embodiments 2 to 2.11, wherein the amount of siponimod in the combination is from 0.25 to 1.5 mg.

Embodiment 2.15: A combination according to any of embodiments 2 to 2.11, wherein the amount of siponimod in the combination is from 0.5 to 1.0 mg.

Embodiment 2.16: A combination according to any of embodiments 2 to 2.11, wherein the amount of siponimod in the combination is 2.0 mg.

Embodiment 2.17: A combination according to any of embodiments 2 to 2.11, wherein the amount of siponimod in the combination is 1.5 mg.

Embodiment 2.18: A combination according to any of embodiments 2 to 2.11, wherein the amount of siponimod in the combination is 1.0 mg.

Embodiment 2.19: A combination according to any of embodiments 2 to 2.11, wherein the amount of siponimod in the combination is 0.5 mg.

Embodiment 2.20: A combination according to any of embodiments 2 to 2.19, wherein siponimod is siponimod hemifumarate.

Embodiment 3: A combination comprising siponimod and laquinimod.

Embodiment 3.1: A combination according to embodiment 3, wherein the amount of laquinimod in the combination is from 0.1 to 10 mg.

Embodiment 3.2: A combination according to embodiment 3, wherein the amount of laquinimod in the combination is from 0.1 to 2.0 mg.

Embodiment 3.3: A combination according to embodiment 3, wherein the amount of laquinimod in the combination is from 0.1 to 1.2 mg.

Embodiment 3.4: A combination according to embodiment 3, wherein the amount of laquinimod in the combination is from 0.1 to 0.5 mg.

Embodiment 3.5: A combination according to embodiment 3, wherein the amount of laquinimod in the combination is from 0.2 to 0.5 mg.

Embodiment 3.6: A combination according to embodiment 3, wherein the amount of laquinimod in the combination is 1.2 mg.

Embodiment 3.7: A combination according to embodiment 3, wherein the amount of laquinimod in the combination is 0.6 mg.

Embodiment 3.8: A combination according to embodiment 3, wherein the amount of laquinimod in the combination is 0.5 mg.

Embodiment 3.9: A combination according to embodiment 3, wherein the amount of laquinimod in the combination is 0.3 mg.

Embodiment 3.10: A combination according to embodiment 1, wherein the amount of laquinimod in the combination is 0.25 mg.

Embodiment 3.11: A combination according to any of embodiments 3 to 3.10, wherein laquinimod is laquinimod sodium.

Embodiment 3.12: A combination according to any of embodiments 3 to 3.11, wherein the amount of siponimod in the combination is from 0.1 to 10 mg.

Embodiment 3.13: A combination according to any of embodiments 3 to 3.11, wherein the amount of siponimod in the combination is from 0.1 to 2.0 mg.

Embodiment 3.14: A combination according to any of embodiments 3 to 3.11, wherein the amount of siponimod in the combination is from 0.25 to 1.5 mg.

Embodiment 3.15: A combination according to any of embodiments 3 to 3.11, wherein the amount of siponimod in the combination is from 0.5 to 1.0 mg.

Embodiment 3.16: A combination according to any of embodiments 3 to 3.11, wherein the amount of siponimod in the combination is 2.0 mg.

Embodiment 3.17: A combination according to any of embodiments 3 to 3.11, wherein the amount of siponimod in the combination is 1.5 mg.

Embodiment 3.18: A combination according to any of embodiments 3 to 3.11, wherein the amount of siponimod in the combination is 1.0 mg.

Embodiment 3.19: A combination according to any of embodiments 3 to 3.11, wherein the amount of siponimod in the combination is 0.5 mg.

Embodiment 3.20: A combination according to any of embodiments 3 to 3.19, wherein siponimod is siponimod hemifumarate.

Embodiment 4: A pharmaceutical composition comprising siponimod and laquinimod and at least one pharmaceutically acceptable carrier.

Embodiment 4.1: A pharmaceutical composition according to embodiment 4, wherein the composition is for oral administration.

Embodiment 4.2: A pharmaceutical composition according to embodiment 4, wherein the composition is a solid composition for oral administration.

Embodiment 4.3: A pharmaceutical composition according to embodiment 4, wherein the composition is a tablet or a capsule.

Embodiment 4.4: A pharmaceutical composition according to any of embodiments 4 to 4.3, wherein the amount of laquinimod in the composition is from 0.1 to 10 mg.

Embodiment 4.5: A combination according to any of embodiments 4 to 4.3, wherein the amount of laquinimod in the composition is from 0.1 to 2.0 mg.

Embodiment 4.6: A combination according to any of embodiments 4 to 4.3, wherein the amount of laquinimod in the composition is from 0.1 to 1.2 mg.

Embodiment 4.7: A combination according to any of embodiments 4 to 4.3, wherein the amount of laquinimod in the composition is from 0.1 to 0.5 mg.

Embodiment 4.8: A combination according to any of embodiments 4 to 4.3, wherein the amount of laquinimod in the composition is from 0.2 to 0.5 mg.

Embodiment 4.9: A combination according to any of embodiments 4 to 4.3, wherein the amount of laquinimod in the composition is 1.2 mg.

Embodiment 4.10: A combination according to any of embodiments 4 to 4.3, wherein the amount of laquinimod in the composition is 0.6 mg.

Embodiment 4.11: A combination according to any of embodiments 4 to 4.3, wherein the amount of laquinimod in the composition is 0.5 mg.

Embodiment 4.12: A combination according to any of embodiments 4 to 4.3, wherein the amount of laquinimod in the composition is 0.3 mg.

Embodiment 4.13: A combination according to any of embodiments 4 to 4.3, wherein the amount of laquinimod in the composition is 0.25 mg.

Embodiment 4.14: A combination according to any of embodiments 4 to 4.13, wherein laquinimod is laquinimod sodium.

Embodiment 4.15: A combination according to any of embodiments 4 to 4.13, wherein the amount of siponimod in the composition is from 0.1 to 10 mg.

Embodiment 4.16: A combination according to any of embodiments 4 to 4.13, wherein the amount of siponimod in the composition is from 0.1 to 2.0 mg.

Embodiment 4.17: A combination according to any of embodiments 4 to 4.13, wherein the amount of siponimod in the composition is from 0.25 to 1.5 mg.

Embodiment 4.18: A combination according to any of embodiments 4 to 4.13, wherein the amount of siponimod in the composition is from 0.5 to 1.0 mg.

Embodiment 4.19: A combination according to any of embodiments 4 to 4.13, wherein the amount of siponimod in the composition is 2.0 mg.

Embodiment 4.20: A combination according to any of embodiments 4 to 4.13, wherein the amount of siponimod in the composition is 1.5 mg.

Embodiment 4.21: A combination according to any of embodiments 4 to 4.13, wherein the amount of siponimod in the composition is 1.0 mg.

Embodiment 4.22: A combination according to any of embodiments 4 to 4.13, wherein the amount of siponimod in the composition is 0.5 mg.

Embodiment 4.21: A combination according to any of embodiments 4 to 4.19, wherein siponimod is siponimod hemifumarate.

Embodiment 5: A kit comprising
(a) laquinimod,
(b) siponimod,
(c) instructions for the simultaneous, separate or sequential use thereof in the treatment of secondary progressive multiple sclerosis, and
(d) at least one container for containing components (a) and (b).

Embodiment 6: A pharmaceutical package comprising a combination comprising siponimod and laquinimod and written instructions for the simultaneous, separate or sequential use thereof in the treatment of secondary progressive multiple sclerosis.

Embodiment 7: Use of a combination comprising siponimod and laquinimod for the treatment, prevention or delay of progression of secondary progressive multiple sclerosis.

Embodiment 8: Use of a combination comprising siponimod and laquinimod for the manufacture of a medicament for the treatment, prevention or delay of progression of secondary progressive multiple sclerosis.

Embodiment 9: A method for the treatment, prevention or delay of progression of secondary progressive multiple sclerosis in a subject in need of such treatment, which comprises administering to said subject a therapeutically effective amount of a combination comprising siponimod and laquinimod.

Embodiment 10: A method for the treatment, prevention or delay of progression of secondary progressive multiple sclerosis in a subject in need of such treatment, which comprises (i) diagnosing said secondary progressive multiple sclerosis in said subject, and (ii) administering to said subject a therapeutically effective amount of a combination comprising siponimod and laquinimod.

The above embodiments are offered to illustrate, but not to limit the present invention.

The invention claimed is:

1. A synergistic combination of laquinimod and siponimod, wherein the amount of laquinimod in the combination is from 0.1 to 1.2 mg and wherein the amount of siponimod in the combination is from 0.1 to 2.0 mg.

2. The combination according to claim 1, wherein the amount of laquinimod in the combination is from 0.2 to 0.5 mg and wherein the amount of siponimod in the combination is from 0.5 to 1.5 mg.

3. A pharmaceutical composition comprising siponimod and laquinimod and at least one pharmaceutically acceptable carrier, wherein the amount of laquinimod in the composition is from 0.1 to 1.2 mg and wherein the amount of siponimod in the composition is from 0.1 to 2.0 mg.

4. The pharmaceutical composition according to claim 3, wherein the amount of laquinimod in the composition is from 0.2 to 0.5 mg and wherein the amount of siponimod in the composition is from 0.5 to 1.5 mg.

5. A method for the treatment or delay of progression of secondary progressive multiple sclerosis in a subject in need of such treatment, which comprises administering to said subject a combination comprising siponimod and laquinimod, wherein the amount of laquinimod in the combination is from 0.2 to 0.5 mg and wherein the amount of siponimod in the combination is from 0.5 to 1.5 mg.

6. A method for the treatment or delay of progression of secondary progressive multiple sclerosis in a subject in need of such treatment, which comprises (i) diagnosing said secondary progressive multiple sclerosis in said subject, and (ii) administering to said subject a combination comprising siponimod and laquinimod, wherein the amount of laquinimod in the combination is from 0.2 to 0.5 mg and wherein the amount of siponimod in the combination is from 0.5 to 1.5 mg.

* * * * *